US005628960A

United States Patent [19]

Beer et al.

[11] Patent Number: 5,628,960

[45] Date of Patent: May 13, 1997

[54] COMPOSITE CELLULOSE NITRATE MEMBRANE ON POLYESTER SUPPORT

[75] Inventors: Hans Beer, Bösinghausen; Klaus Froese, Hardegsen, both of Germany

[73] Assignee: Sartorius AG, Goettingen, Germany

[21] Appl. No.: 527,378

[22] Filed: Sep. 13, 1995

[30] Foreign Application Priority Data

Oct. 27, 1994 [DE] Germany .......................... 44 38 381.9

[51] Int. Cl.$^6$ .................................................... B01D 39/14

[52] U.S. Cl. ....................... 422/56; 422/101; 210/500.22; 210/500.29; 210/500.3

[58] Field of Search ................................. 422/56–58, 61, 422/101; 210/500.29, 500.3, 500.22, 490

[56] References Cited

U.S. PATENT DOCUMENTS

| | | | |
|---|---|---|---|
| 4,333,972 | 6/1982 | Kesting | 427/244 |
| 5,004,543 | 4/1991 | Pluskal et al. | 210/490 |
| 5,350,694 | 9/1994 | Zimmerle | 436/2 |

*Primary Examiner*—Lyle A. Alexander
*Attorney, Agent, or Firm*—Chernoff, Vilhauer, McClung & Stenzel

[57] ABSTRACT

There is disclosed a composite isotropic cellulose nitrate membrane on a polyester support and a method of making the same, the membrane having particular utility as various types of reagent-containing test strips for use in analytical chemistry and medicinal diagnostics.

6 Claims, 1 Drawing Sheet

ST AVAILABLE CO

ST AVAILABLE CO

MPOSITE CELLULOSE NITRATE BRANE ON POLYESTER SUPPORT

CKGROUND OF THE INVENTION ition concerns a microporous isotropic cellulose ") membrane on a polyester support which finds in the production of sorbent reactants, in est strips for use in analytical chemistry and iagnostics, and to a process for the manufacture embrane.

se of composite membranes reinforced by film ecial challenges arise in regard to their required cs. The membrane must be durably adhered to port and must not separate therefrom during essing or in the course of its use. Ample hydro- the membrane must be maintained throughout e and during the course of use. Unless such cs are met, reproducibility of analytical and esults cannot be guaranteed. Furthermore, in alyses and diagnostic examinations to proceed supported membrane must exhibit a high lateral elocity for the liquids tested. "Lateral migration eans the speed with which a liquid introduced to of a membrane spreads in a direction generally the support film, and is expressed in units of nm/min.

e supported membranes used as sorbent test alytic and diagnostic procedures are known. ent No. 34 07 359 describes a supported mem- rising an asymmetric membrane upon a macro- mooth polyester film made by coating the poly- t with a polymeric casting solution comprising , polyether carbonates, polyacrylic nitriles or es, whereby the polymeric coating is deposited ort by phase inversion. A primary drawback of brane lies in the unsatisfactory adhesion of the o the support. Although German Patent No. 40 closes a method of achieving a more lasting tween an asymmetric polyurethane membrane rt, the method comprising the use of a special nd support having a roughened surface treated -static solution, this approach is relatively com- stly. Another serious drawback of asymmetric is that the asymmetric structure leads to a lateral elocity gradient for liquids introduced to the whereby liquid moves faster in the zone of the ter pores (those adjacent the support) than in the smaller diameter pores (those on the opposite nembrane). Because of this gradient, use of such membrane as a sorbent test strip often yields xact and difficultly reproducible indications for being tested.

of its good adsorption characteristics, particu- spect to substances containing protein, CN is a membrane material for sorbent reactants. o durable adhesion of a pure CN membrane on support may be expected from a mere casting of ne on the polyester support. European Patent No. describes an approach to securing a CN mem- support, namely, a porous laminated CN mem- ued to a polyester support film by a layer of he chief disadvantage of such a membrane is that ves of this type, as storage time increases, a loss on potential and of the hydrophilicity of the layer can occur, because the adhesive migrates mbrane and reacts with surfactant which is also present in the membrane. Moreover, the fabrication of such laminated membranes and gluing of the same to the supports is a costly multi-step process. Lamination of CN membranes by merely using heat and pressure is not possible both because no durable adhesion is achieved and because it causes the CN membrane to become partially compacted, resulting in a substantial loss in the membrane's lateral migration velocity.

A principal object of the present invention, therefore, is the provision of a composite microporous CN membrane on a polyester support wherein the CN membrane is bonded durably to the support and which exhibits no lateral migration gradient, all without the use of heat, pressure or adhesives. A further object is to provide an economical procedure for the production of such a composite membrane. These objects and others will become apparent upon consideration of the invention, which is summarized and described in detail below.

SUMMARY OF THE INVENTION

The essence of the present invention lies in providing an adsorbent membrane comprising a polymeric blend of CN and cellulose acetate ("CA") theft has an isotropic structure. Such a membrane is produced by a phase inversion process following an evaporative procedure, wherein care is taken to ensure that the membrane is free from filter dust.

DETAILED DESCRIPTION OF THE INVENTION

Figure 1A:
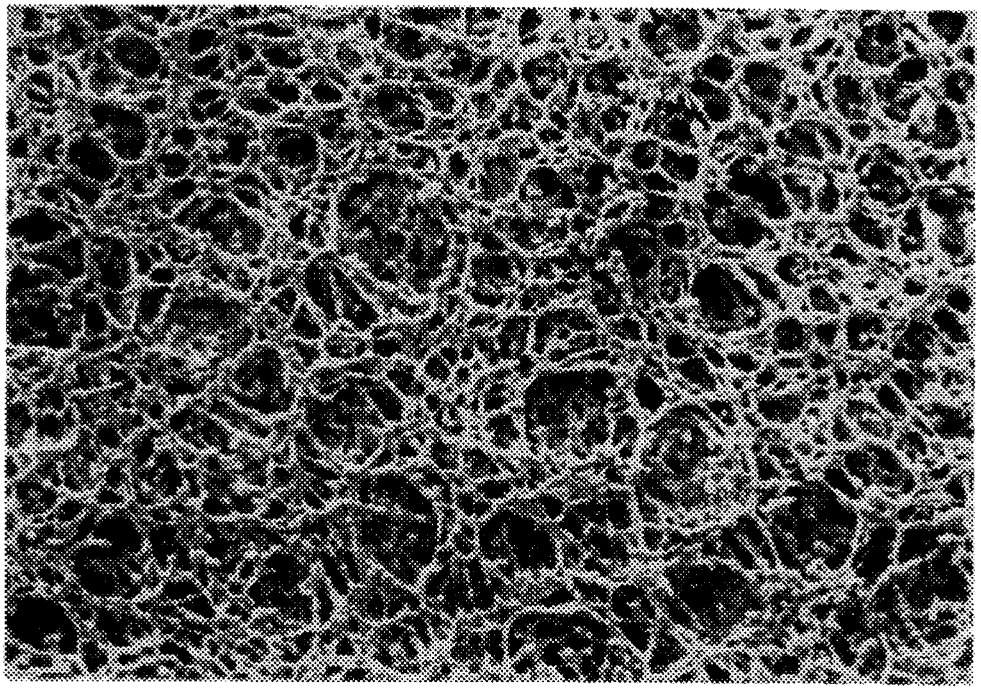
FIGS. 1*a* and 1*b* are scanning electron photomicrographs (SEMs) of an exemplary membrane of the present invention.

According to the present invention, it has been discovered that a durable adhesion of an absorbent isotropic CN membrane to a polyester film support may be achieved by casting the membrane from a polymer blend of CN with small quantities of CA. Rather surprisingly, the affinity of such a CN/CA membrane to the polyester support is so great, that no pretreatment of the support or use of any adhesive or any other means for adhesion is required. Since the membrane is directly bonded to the film support, the danger of migration of foreign material into the composite membrane is excluded from the outset. It has further been discovered that with the small portion of CA employed in the polymer blend, the desirable characteristics of CN for use with sorbent reactants, such as good adsorption ability and rapid lateral migration velocity, remain intact. The preferred portion of CA in the polymer blend relative to CN is from 0.5 to 10 wt %, more preferably from 1 to 5 wt %. Since such composite membranes have an isotropic structure, they exhibit virtually no lateral migration velocity gradients. Liquids brought in contact with such membranes spread with nearly uniform lateral speed, completely penetrating the membrane and moving in a plane that is perpendicular to the face of the membrane. Thus, by use of such membranes as sorbent reactant test strips, sharp and highly reproducible imaging of the material to be tested is obtained.

It has also been found that so-called "filter dust" is also partly responsible for the appearance of fuzzy and poorly reproducible imaging on the tested materials, which is generally encountered in the surface areas of the membranes. Filter dust forms during the production of the membrane from non-membrane-forming components of the raw materials used which mainly consist of sub-molecular cellulose derivatives. The tendency toward the formation of filter dust is especially pronounced in the case of membranes with large pore diameters—between 0.45 and 15 µm—which is the pore diameter range preferably employed for sorbent reactants because lateral migration velocity increases with the increase in pore size. Membranes prepared in accordance with the present invention have proven to be free of such filter dust imperfections.

In a particularly preferred embodiment, a wetting agent or surfactant is introduced to the membrane, either as a component of the CN/CA membrane casting solution, or by injection into the membrane after casting. The amount of surfactant included in the casting solution is preferably in an amount that, upon contact of the test liquid with color indicators such as test reagents in the membrane, an enhanced or sharpened image appears; this phenomenon is particularly helpful if the test reagent is laid out in the membrane in a regular pattern, such as points, lines or cross-hatching. A preferred class of surfactants are the alkyl sulphonates, having alkyl groups containing from 12 to 18 carbon atoms, most preferably averaging 15 carbon atoms.

Depending upon pore size, a membrane of the present invention can reach a lateral migration velocity for water of from 26 mm/5 min (pore diameter 0.45 µm) to 82 mm/5 min (pore diameter 10 µm), measured according to vertical absorption analog DIN 53106.

The composite CN membranes of the present invention are preferably made by a phase inversion evaporation process and are thereby precipitated directly onto the support film. To this end, the untreated support film is coated with the casting dope, comprising CN and CA in suitable solvents, such as methyl acetate, ethanol, and butanol with low water content, followed by evaporation of the volatile components. For the production of hydrophilic membranes, surfactant is preferably added to the casting dope. For the provision of filter dust-free membranes, one should follow the treatment set forth in German Patent No. 37 08 946, generally comprising dissolution of the polymer blend, followed by reprecipitation. The support film preferably comprises untreated, optically clear polyethylene terephthalate having a thickness of from 50 to 175 µm, most preferably from 100 to 150 µm.

EXAMPLE 1

Figure 1B:
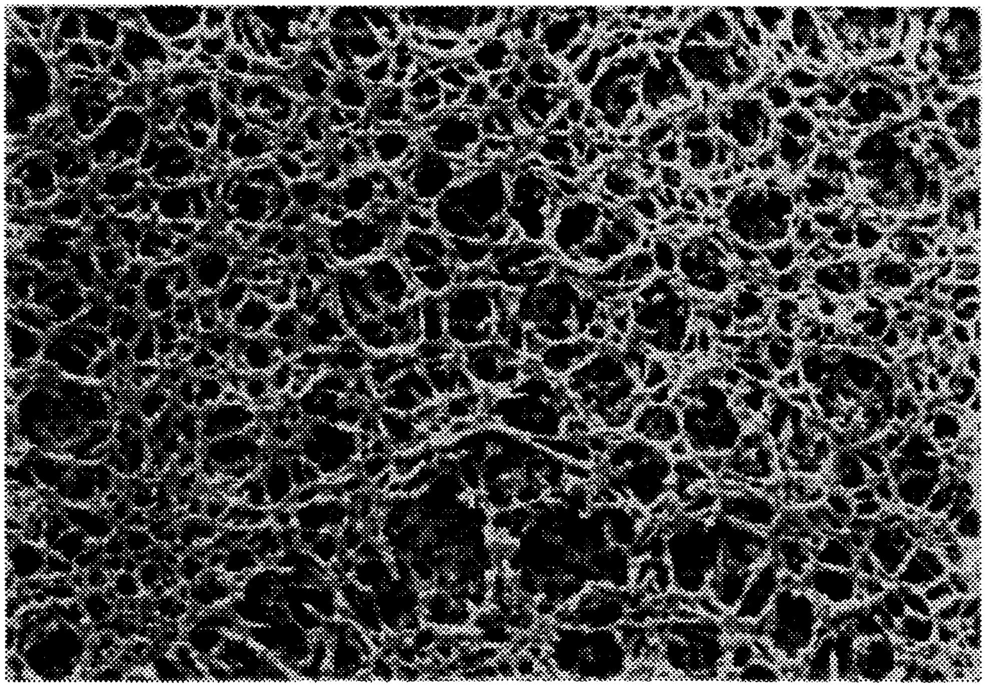

A polymeric blend solution was prepared consisting of 8.8 wt % CN, 0.2 wt % CA, 45.3 wt % methyl acetate, 32.8 wt % ethanol and 12.9 wt % 2-butanol (total 100 wt %). To this polymeric blend solution 9.2 wt % water (relative to the 100 wt %) was added to form a casting dope. Prior to adding the cellulose derivatives to the polymeric blend solution, they were first dissolved in acetone and methylene chloride and reprecipitated by the addition of methanol and water to remove extraneous non-membrane-forming substances which are responsible for the creation of "filter dust." In a covered tensioning machine, the casting dope was coated on an untreated support film of 800 µm-thick polyethylene terephthalate; the volatiles were then evaporated at temperatures between 15° and 25° C. to bring about phase inversion, causing the formation of a CN membrane of isotropic structure with a pore size of 8 µm. FIGS. 1*a* and 1*b* are 500×SEMs of cross sections of the membrane produced. FIG. 1*a* shows the top side of the membrane, while FIG. 1*b* shows the underside of the membrane that is in contact with the support film. The support film itself is not visible. The isotropic structure of the membrane is evident in both FIGS. 1*a* and 1*b*.

EXAMPLES 2–4

Example 1 was repeated with the exceptions that 0.01 wt % surfactant (sodium alkyl sulphonate having an average alkyl chain of 15 carbons) and 6.5 wt % water (Example 2) and 10 wt % water (Example 4) were added to the casting dope solution. Membranes having an isotropic structure and pore sizes between 1 and 10 µm and with excellent lateral migration velocity were obtained. The results are summarized in the following table.

| - | Water | Average Pore Diameter | Lateral Migration Velocity | |
|---|---|---|---|---|
| Ex. No. | (wt %) | (µm) | mm/5 min | mm/2 min |
| 2 | 6.5 | 0.45 | 26 | 17 |
| 3 | 9.2 | 8.00 | 68 | 45 |
| 4 | 10.0 | 10.00 | 82 | 54 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composite microporous cellulose nitrate membrane comprising a polymeric blend of cellulose nitrate and cellulose acetate cast from a casting solution onto a polyester support which, after casting, exhibits an isotropic structure wherein said casting solution comprises 6 to 13 wt % water added to a polymeric blend solution comprising the following components in the approximate weight percentage noted:

| | |
|---|---|
| cellulose nitrate | 5–15 wt % |
| cellulose acetate | 0.075–0.5 wt % |
| ethanol | 20–40 wt % |
| butanol | 5–15 wt % |
| methyl acetate | balance. |

2. The membrane of claim 1 wherein said polymeric blend solution comprises the following components in the weight percentages noted:

| | |
|---|---|
| cellulose nitrate | 8.8 wt % |
| cellulose acetate | 0.2 wt % |
| ethanol | 32.8 wt % |
| 2-butanol | 12.9 wt % |
| methyl acetate | 45.3 wt % |
| sodium alkyl sulfonate | 0.01 wt %. |

3. The membrane of claim 1 wherein said cellulose nitrate component and said cellulose acetate component of said polymeric blend solution have been dissolved and reprecipitated prior to inclusion in said polymeric blend solution.

4. The membrane of claim 1 wherein said membrane is hydrophilic and contains a surfactant.

5. The membrane of claim 4 wherein said surfactant comprises a sodium alkyl sulphonate containing from 12 to 18 carbon atoms.

6. The membrane of claim 5 in the form of a test strip.

* * * * *

UNITED STATES PATENT AND TRADEMARK OFFICE
CERTIFICATE OF CORRECTION

PATENT NO. : 5,628,960

DATED : May 13, 1997

INVENTOR(S) : Beer et al.

It is certified that error appears in the above-indentified patent and that said Letters Patent is hereby corrected as shown below:

Col. 2, line 23, change "theft" to --that--

Signed and Sealed this

Second Day of December, 1997

Attest:

BRUCE LEHMAN

*Attesting Officer* *Commissioner of Patents and Trademarks*